United States Patent
Zhang

(10) Patent No.: US 11,702,655 B2
(45) Date of Patent: Jul. 18, 2023

(54) METHOD FOR TREATING CANCER BY DISABLING-BRCA1/FANCM INTERACTION

(71) Applicant: NEW YORK INSTITUTE OF TECHNOLOGY, Old Westbury, NY (US)

(72) Inventor: Dong Zhang, Old Westbury, NY (US)

(73) Assignee: NEW YORK INSTITUTE OF TECHNOLOGY, Old Westbury, NY (US)

( * ) Notice: Subject to any disclaimer, the term of this patent is extended or adjusted under 35 U.S.C. 154(b) by 408 days.

(21) Appl. No.: 16/074,313

(22) PCT Filed: Feb. 15, 2017

(86) PCT No.: PCT/US2017/017863
§ 371 (c)(1),
(2) Date: Jul. 31, 2018

(87) PCT Pub. No.: WO2017/146947
PCT Pub. Date: Aug. 31, 2017

(65) Prior Publication Data
US 2021/0180056 A1 Jun. 17, 2021

Related U.S. Application Data

(60) Provisional application No. 62/298,189, filed on Feb. 22, 2016.

(51) Int. Cl.
*C12N 15/113* (2010.01)
*C07K 16/00* (2006.01)

(52) U.S. Cl.
CPC ............ *C12N 15/113* (2013.01); *C07K 16/00* (2013.01); *C12N 2310/14* (2013.01)

(58) Field of Classification Search
None
See application file for complete search history.

(56) References Cited

U.S. PATENT DOCUMENTS

| | | |
|---|---|---|
| 2012/0329047 A1 | 12/2012 | Reddel et al. |
| 2013/0090370 A1 | 4/2013 | Takagi |
| 2013/0331365 A1 | 12/2013 | Lee |

OTHER PUBLICATIONS

Fathiya Al Murshedi, Role of FANCM in Telomere Maintenance in Alternative Lengthening of Telomeres (ALT) Human Cells (2010).

Masters thesis. https://www.collectionscanada.gc.ca/obj/thesescanada/vol2/002/MR67520.PDF?is_thesis=1&oclc_number=796917441. Retrieved from Internet [retrieved Feb. 3, 2022]) (Year: 2010).*
Gao et al., Targeting of DNA Damage Signaling Pathway Induced Senescence and Reduced Migration of Cancer cells. Journals of Gerontology: Biological Sciences (2015), 701-713 (Year: 2014).*
Ono et al., Analysis of Human Protein Replacement Stable Cell Lines Established using snoMEN-PR Vector, PLOS ONE (2013), 8(4), e62305, 1-12 (Year: 2013).*
Henson et al., Alternative lengthening of telomeres in mammalian cells. Oncogene (2002) 21, 598-610. (Year: 2002).*
Nguyen et al., Chemistry and Biology (2013), 20: 55-62 (Year: 2013).*
Marschall et al., Antibodies inside of a cell can change its outside: Can intrabodies provide a new therapeutic paradigm? Computational and Structural Biotechnology Journal (2016), 14: 304-308 (Year: 2016).*
Marschall et al., Specific in vivo knockdown of protein function by intrabodies. mAbs (2015), 7(6): 1010-1035 (Year: 2015).*
Temime-Smaali et al., Topoisomerase IIIa is required for normal proliferation and telomere stability in alternative lengthening of telomeres. EMBO Journal (2008), 27: 1513-1524 (Year: 2008).*
Malhotra et al., Small interfering ribonucleic acid design strategies for effective targeting and gene silencing. Expert Opinion on Drug Discovery (2011), 6(3): 269-289 (Year: 2011).*
Patel et al., Exploiting synthetic lethality to target BRCA1/2-deficient tumors: where we stand. Oncogene (2021) 40: 3001-3014 (Year: 2021).*
Murshedi: "Role of FANCM in Telomere Maintenance in Alternative Lengthening of Telomeres (ALT) Human Cells", A Thesis for Degree of Master, 2010, XP055411329, Retrieved from the Internet [retrieved on Mar. 21, 2017].
Samir Acharya, et al., "Association of BLM and BRCA1 during Telomere Maintenance in ALT Cells," PLOS One, vol. 9(8), pp. e103819, 2004.
Rebekka A. Schwab, et al., "ATR activation and replication fork restart are defective in FANCM-deficient cells," EMBO J., vol. 29(4). pp. 806-818 (2010).
Dimitrios J. Stavropoulos, et al., "The Bloom syndrome helicase BLM interacts with TRF2 in ALT cells and promotes telomeric DNA synthesis," Human Molecular Genetics, vol. 11(25). pp. 3135-3144 (2002).

(Continued)

*Primary Examiner* — Samuel C Woolwine
*Assistant Examiner* — Catherine Konopka
(74) *Attorney, Agent, or Firm* — Amster, Rothstein & Ebenstein LLP

(57) ABSTRACT

The method involves an approach of inhibiting replication of dysfunctional cells which adopt alternative lengthening of telomeres, or "ALT." The methodology involves inhibition of Fanconi anemia complementation group M (FANCM), and one or both of breast cancer 1 (BRCA1) and Bloom syndrome protein (BLM). These molecules are the keys to the elimination of replication stress caused by ALT. In other words, they permit the dysfunctional cells to proliferate. Inhibition of these molecules inhibits proliferation.

3 Claims, No Drawings

(56) References Cited

OTHER PUBLICATIONS

Priyanka Verma, et al., "Noncanonical views of homology-directed DNA repair," Genes & Development, vol. 30(10), pp. 1138-1154 (2016).
Xiaolei Pan, et al., "FANCM, BRCA1, and BLM cooperatively resolve the replication stress at the ALT telomeres," www.pnas.org/cgi/doi/10.1073/pnas.1708065114, PNAS, pp. E5940-E5949 (Jul. 3, 2017).
International Search Report from PCT/US17/17863 dated May 26, 2017.

* cited by examiner

METHOD FOR TREATING CANCER BY DISABLING-BRCA1/FANCM INTERACTION

FIELD OF THE INVENTION

This invention relates to a method for alleviating a condition characterized by dysfunctional cells, where the dysfunction itself is characterized by cells using the alternative lengthening of telomeres, or "ALT", as the way to maintain their telomeres. More specifically, it relates to inhibiting replication stress response or destruction of, said cells by inhibiting expression of FANCM, and one or both of BRCA1 and BLM, all of which are involved in replication stress response in ALT cells.

BACKGROUND AND PRIOR ART

Faithful replicating of the genome is vital for mammalian cells. The "replisome" (the DNA replication machinery) of the cell frequently encounters impediments during replication. The term "replication stress" is used to describe temporary or transient stalling of the replication fork (see, e.g., Berti, et al., Nat. Struct. Mol. Biol., 23(2):103-109 (2016); Zeman, et al., Nat. Cell Biol., 16(1):2-9 (2004)).

One of the endogenous regions of DNA which poses challenges to the replisome is the telomere. This structure consists of tandem repeats of the DNA sequence $(TTAGGG)_n$ located at the end of every linear chromosome. Telomerase catalyzes the additional of this sequence to the end of the chromosomes. The telomeres vary in length from 10-15 Kb in humans, and 25-50 Kb in mice.

With few exceptions, somatic cells do not express telomerase, and undergo progressive telomere shortening with each cell cycle, eventually leading to senescence, and cell death. See, e.g., Lopez-Ortin, et al., Cell, 153(6):1194-1217 (2013).

Dysfunction of cells, like cancer cells, is sometimes characterized by replicative immortality. See, e.g., Hanahan, et al., Cell, 144(5):646-674 (2011). This "replicative immortality" is achieved by overcoming telomere shortening. A percentage of these dysfunctional cells do so by utilizing homologous recombination based lengthening of telomeres. See, Dilley, et al., Trends in Cancer, 1(2):145-156 (2015); Cesare, et al., Nat. Rev. Genet., 11(5):319-330 (2010). Cells using this "alternative lengthening of telomeres" ("ALT" hereafter) are prone to susceptibility to replicative stress. Nonetheless, ALT cells, i.e., cells which maintain their telomere length via the above referenced method, do undergo replication, as is evident from, e.g., cancer cells which acquire ALT. (It should be noted that various methodologies are well known for determining if a cell is an ALT cell).

Clearly, there is a mechanism for overcoming the replicative stress experienced by ALT cells, which enables their continued replication, notwithstanding the defect, or other defects associated with the ALT cells.

FANCM is a recognized member of the Fanconi Anemia ("FA") family of genes. The members of this family are recognized, inter alia, as being involved in repairing interstrand cross linking lesions. See, e.g., Caccaldi, et al., Nat. Rev. Mol. Cell Biol., 17(6):337-349 (2016); and Michl, et al., EMBO J., 35(9):909-923 (2016), both of which are incorporated by reference. Information on FANCM and its three obligatory binding partners (FAAP24, MHFI, and MHF2), can be found at, e.g., Meetei, et al., Nat. Genet., 37(9):958-963 (2005); Mosedale, et al., Nat. Struct. Mol. Biol., 12(9):763-771 (2005); Ceccia, et al., Mol. Cell, 25(3): 331-343 (2007); Yam, et al., Mol. Cee, 37(6):854-878 (2010); Singh, et al., Mol. Cell, 37(6):879-886 (2010); Collis, et al., Mol. Cell, 32(3):313-324 (2008); Huang, et al., Mol. Cell, 52(3):434-446 (2013); Huang, et al., Mol. Cell, 39(2)):259-268 (2010); and Wang, et al., Mol. Cell, 49(5): 997-1009 (2013). Also see, Schwab, et al., EMBO J., 29(4):806-818 (2010); Luke-Glaser, et al., EMBO J., 29(4): 795-805 (2010); Singh, et al., Blood, 114(1):174-180 (2009); and Blackford, et al., Hum. Mol. Genet., 21(9): 2005-2016 (2012).

Collis, et al., supra, have observed that acute depletion of FANCM in unperturbed human cancer cells causes increased formation of γ-H2AX foci, a common marker for DNA damage. Schwab, et al., supra, observed this in chicken DT40 cells as well.

Neither of Collis nor Schwab pinpointed the cause or nature of DNA damage in these cells, nor have other investigators.

It has now been found that depletion of FANCM, or one of its obligate binding partners induces replication stress in ALT cells, primarily taken place at the telomeres. Deletion of FANCM was shown to dramatically reduce replication efficiency at these ALT telomeres.

Further, it was found that BLM and BRCA1, both of which are critical proteins for homologous recombination, are recruited to the site of replication stress and help to resolve it by stimulating DNA end resection and promoting homologous recombination.

Codepletion of FANCM and one of BLM or BRCA1 dramatically increases micronuclei formation and increases synthetic lethality.

Hence, it is an object of the invention to develop a method for reducing the number of defective ALT cells in a subject by depleting or reducing expression of FANCM, and one or both of BLM and BRCA1.

How this and other aspects of the invention are achieved will be seen in the disclosure which follows:

EXAMPLE 1

This first set of experiments were designed to confirm that DNA damage seen in FANCM deficient cells was in fact due to replication stress, in contrast to double strand DNA breaks.

Each of these activates a different pathway, i.e., replication stress activates the ATR-DNA-PKcs-Chk1 pathway, while double strand breaks activate the ATM-ChK2 pathway. See, e.g., Marichal, et al., Cold Spring Harb. Perspect Biol., 5(9) (2013); and Ceccia, et al., Mol. Cell, 40(2):179-204 (2010).

Further, Ser 345 of ChK1 ("ChKpS345") and Ser33 of RPA ("RPA32-pS33") are phosphorylated by ATR, while Ser4 and Serb of RPA32 ("RPA32-pS4pS8 or pRPA32") are phosphorylated by DNA-PK.

U2-OS and SaOS-2 cells, available from the American Type Culture Collection, are human ALT cells. HeLa and MG63 cells discussed infra, are not. All cells were cultured in DMEM supplemented with 10% FBS, penicillin and streptomycin, at 37° C. in a humidified incubator with 5% $CO_2$.

The cells were depleted of FANCM using siRNA. To elaborate, cells were transfected with siRNA targeting luciferase as a negative control, or two different siRNA molecules which target FANCM. These siRNA molecules are commercially available and were purchased from Dharmacon. Human cells do not express luciferase, and hence the added siRNA should not deplete any genes. Hence, the negative control becomes normal conditions for the experiments which follow. See supra for the standard cultivation conditions. These cells were then contacted with antibodies labeled with a green dye which recognize γH2AX, ChK1-pS345, RPA32-pS4S8, or BLM. All cells were also stained with DAPI which is blue. All antibodies were either purchased, or provided by other investigators. Over 200 cells were counted in each sample.

The results indicated that the luciferase control cells exhibit less than 1% ChK1-pS345 and RPA32-pS4pS8 foci, as compared to controls.

In contrast, when cells were depleted of FANCM with siRNA, approximately 15% of the cells exhibited bright foci containing the above referenced markers. In addition to the increase in RPA-pS4pS8 foci, immunoblotting studies showed a dramatic increase in both RPA32-pS33 and RPA-pS4pS8, indicating that the cells were under replicative stress.

These results suggest that DNA damage in FANCM deficient cells, is mainly due to DNA replication stress.

The results demonstrate that 20-30% of the cells stained positive for BLM. BLM is a DNA helicase which is involved in several crucial steps of the homologous recombination discussed supra.

EXAMPLE 2

These experiments were designed to determine if the replication stress observed in Example 1 was taking place at the telomeres.

Cells depleted of FANCM as discussed supra were probed with three telomere specific markers as were control cells also as described supra. TelC, a peptide nucleic acid probe, TRF1 and TRF2, both of which are key components of the Shelterin complex.

Cells were co-stained with the same ChK1-pS345 antibody used supra together with the DNA probe, or an antibody specific to TRF1, or one specific to TRF2.

In parallel experiments, the ChK1-pS345 antibody was substituted by one specific for BLM.

The results indicated that the foci resulting from staining all colocalized with the telomeric markers, and they were bigger and brighter than normal telomeric staining, suggesting clustering at telomeres experiencing replicative stress.

When these experiments were repeated in ALT cell SaOS-2, similar results were obtained. In contrast, when telomerase positive cells HeLa and MG63 were tested, the results did not correlate.

These data, collectively, suggest that FANCM functions to alleviate replicative stress at the telomeres of ALT cells.

Further, telomeric foci which colocalize with the other foci tend to be larger and brighter than normal foci, suggesting replication stress. This pattern was repeated in a second set of experiments, with cells of cell line Saos-2, also purchased from the ATCC.

EXAMPLE 3

As noted supra, various functions of FANCM require three obligatory binding partners: FAAP24, MHF1, and MHF2. Also, noted supra, FANCM is part of a family of FA proteins.

To review their functions, FAAP24 binds the C terminus of FANCM, and works as part of the FA core complex, to promote monoubiquination of FANCD2 and FANCI (ID2). MHF1 and MHF2 are both histone fold proteins and form stable, stochiometric heterodimers, referred to as "MHF1/2." The dimer binds the N-terminus of FANCM, and also functions as in the manner of FAAP24. Experiments were carried out to determine if these molecules or other members of the FA family acted similarly to FANCM.

U2-OS cells were transfected, with siRNA that either targeted luciferase, or with two siRNAs, "FAAP24-1 and -2". Transfected cells were costained with an antibody recognizing ChK1-pS345, or BLM, as described supra, together with either a PNA probe recognizing the G rich strand of telomeres, or a TRF1 specific antibody. Cells were counted as in the prior examples.

These two siRNA molecules deplete the same gene, but two were used in order to eliminate the so-called "off target" effect. In brief, although siRNA (generally 19-27 nucleotides long) is chosen to be specific to only one gene, there are situations where the siRNA depletes a gene in addition to the one targeted. Using the two molecules serves to minimize the off-target effect.

The results show that depletion of FAAP24 induced a dramatic increase in ChK1-pS345 and BLM foci. Further, deletion of one or both of MHF1 or MHF2 had the same effect. Deletion of MHF1/2, however, induced fewer relevant foci, suggesting that FAAP24 has the more important role in relieving replication stress. Depletion of all of FANCM, FAAP24, MHF1 and MHF2 had an additive effect, i.e., there was a moderate increase in foci at the telomeres.

Tests on other FA proteins (i.e., FANCB, FANCG, and FANCI), comparable to those discussed supra for FANCM, showed the depletion of FANCI had no impact on foci formation, and deletion of FANCB and FANCG had a moderate, but much reduced role in foci formation. There was a moderate increase in ChK1-pS345 foci formation, not as large as the increase resulting from deletion of FANCM; however, the increase in BLM foci was equivalent to FANCM, suggesting that the FA core complex, could have an active role in inhibiting BLM recruitment.

EXAMPLE 4

These experiments examine the role of FANCM in telomere replication. SMARD assays were carried out, following Drosopoulos, et al., J. Cell Biol., 197(2):253-266 (2012), incorporated by reference, in the subtelomeric regions of FANCM depleted cells. ("SMARD" is an acronym for "single molecule analysis of replicated DNA"). To elaborate, cells were transfected with siRNA, as discussed supra, to deplete FANCM. Then, the cells were pulse labeled with IdU and CldU for 4 hours each, in sequence. After the labeling, the genomic DNA of the cells was digested, subjected to pulsed field gel electrophoresis to separate it, and any genomic DNA enriched in subtelomeres and telomeres was identified using a telomeric specific PNA probe and classic Southern blotting.

Next, the thus identified DNA was stretched and stained with anti-IdU and anti-CldU antibodies, labeled red and green, and classic FISH methodologies. The images were visualized and fibers containing the halogenated nucleotides counted, using standard methods.

The results showed a three-fold decrease in replication efficiency in FANCM depleted cells. The decrease is not believed correlatable to decreases in overall DNA replication because comparison of the cell cycle profile of the FANCM depleted cells was comparable to controls.

These results do, however, support the conclusion that when FANCM is absent or reduced, replication forks tend to pause and/or stall at ALT telomeres, resulting in increased replication stress.

EXAMPLE 5

"BLM" is known to be involved in a number of DNA metabolic pathways including replication, replication stress response, and telomere biology. See, Bizard, et al., Cold Spring Harb. Perspect. Biol., 6(7):a016477 (2014); and Crouteau, et al., Annu. Rev. Biochem., 83:519-552 (2014). It is known to play an important role in DNA end resection during homologous recombination, at telomeres. See, e.g., Gravel, et al., Genes Dev., 22(20:2767-2722 92008); and Kibe, et al., Mol. Cell, 61(2):236-246 (2016).

To study BLM's function, cells were co-depleted of FANCM and BLM, using the siRNA methodology discussed supra, and DNA end resection was monitored via immuno-blotting, using antibodies which recognize RPA32-pS4pS8 and RPA32-pS33.

The depletion of BLM dramatically attenuated DNA end resection in cells also depleted of FANCM, proving that BLM is required for DNA end resection during replication response at ALT telomeres. It should be pointed out that, e.g., Cesare, et al., Nat. Rev. Genet., 11(5):319-330 (2010) show that ALT cells rely on homologous recombination to maintain telomere length and to repair stalled replication forks. Reduced DNA end resection compromises the homologous recombination, and hinders DNA repair processes. The results of this experiment are consistent with an observed, dramatic increase of cells with micronuclei when the two subject molecules were depleted. Further, standard crystal violet assays showed a strong lethal interaction—resulting from the depletion of the two molecules.

EXAMPLE 6

These experiments were designed to determine if BRCA1, another "player" in DNA metabolism, is involved in the ALT telomere replication stress system. This molecule is well known as being very involved in several facets of DNA metabolism, including checkpoint activation, and homologous recombination. Acharya, et al., Phos One, 9(8): 103819 (2014), showed that it was found at ALT telomeres, and that it stimulated helicase activity of BLM.

To study the role of BRCA1, FANCM depleted cells, as described supra, were co-stained with a BRCA1 specific antibody, and telomere specific probes also as described supra. Both U2-OS and SaOS-2 cells were tested using standard methods.

The results showed that a small percentage of control cells showed BRCA1 foci, but these rarely colocalize with telomeres.

On the other hand, over 90% of BRCA1 specific foci in the FANCM depleted cells, colocalize with telomeres.

Of particular interest is that recruitment of BLM and BRCA1 to stressed ALT telomeres, is mutually dependent.

EXAMPLE 7

Further experiments were carried out to elucidate the function of BRCA1 in the repair processes under consideration. It is known that, during repair of double strand breaks ("DSBs"), BRCA1's most important function is to counter 53BP1, and to stimulate DNA end resection so that DSBs can be repaired via homologous recombination, which is recognized as the "high fidelity" repair pathway. It's also been shown that when cells are subjected to the replication stress inducer ultraviolet light, BRCA1 promotes DNA end resection.

The experiments which follow showed that BRCA1 has a role in DNA end resection at telomeres, in FANCM deficient ALT cells.

As with the other examples set forth herein, US-OS cells were transfected with siRNA targeted to luciferase (control), BRCA1, FANCM, or to both BRCA1 and FANCM. Cells were lysed and lysates were blotted with antibodies in accordance with standard methods.

The results indicate that codepletion of BRCA1 and FANCM severely impedes phosphorylation of RPA32 at Ser4/8 and 33, showing that BRCA1 is required for DNA end resection at ALT telomeres.

RPA is known to be involved in repair of damaged DNA. Once the RPA is phosphorylated at Ser4 and Ser8, the thus phosphorylated RPA molecule is recruited to the site of damage, and binds the single stranded DNA.

Thus, measurement of phosphorylation of RPA is an indication of RPA activation, and of DNA end resection—which in turn is an indication of how much single strand DNA has been produced. One therefore determined the amount of repair that is going on in FANCM depleted, ALT cells. Expressed more simply, a decrease in phosphorylated RPA levels suggests reduced DNA end resection and reduced DNA repair.

Further, as was the case with BLM, there was a very dramatic increase in micronuclei in codepleted cells, and strong synthetic lethality in the ALT cells tested, phenomena not seen in telomerase positive cells HeLa and MG63, which do not show ALT features. Nor was synthetic lethality seen when BRCA1 and BLM1 were codepleted, while FANCM was not.

The foregoing disclosure sets forth features of the invention, which involves methods for eliminating dysfunctional ALT cells, by inhibiting FANCM, as well as one or both of BRCA1 and BLM. These three molecules (FANCM, BRCA1, and BLM), are shown to be involved in alleviating replication stress in ALT cells. By inhibiting them, the viability of these dysfunctional cells is dramatically reduced.

The inhibition can be at the nucleotide level using, e.g., siRNA or other inhibitors of protein expression, but also can take place at the protein level, by using protein inhibitors, such as small molecules, i.e., non-peptide based, heterocyclic molecules, inhibiting antibodies, antibody fragments which are inhibitory, and so forth.

The methodology may be used in combination with other methodologies for inhibiting and/or eliminating dysfunctional cells. For example, several types of cancer cells are characterized by ALT. By inhibiting the mechanism which alleviates the ALT, standard drug therapies can be modified to, e.g., reduce the strain on normal cells caused by severe therapies. Such severe forms of therapy are no longer needed when the repair mechanism is inhibited.

Other aspects of the invention will be clear to the skilled artisan and are not set forth here.

The teens and expression which have been employed are used as terms of description and not of limitation, and there is no intention in the use of such terms and expression of excluding any equivalents of the features shown and described or portions thereof, it being recognized that various modifications are possible within the scope of the invention.

The invention claimed is:

1. A method for inhibiting replication of Alternative Lengthening of Telomeres (ALT) cells comprising contacting said ALT cells with an siRNA inhibitor of FANCM and an siRNA inhibitor of BRCA1 in an amount sufficient to inhibit FANCM and BRCA1, respectively.

2. The method of claim 1, wherein said ALT cells are cancer cells.

3. The method of claim 1, wherein said siRNA molecules consist of 19-27 nucleotides.

* * * * *